United States Patent [19]

Kurihara

[11] 4,160,266

[45] Jul. 3, 1979

[54] X-RAY TELEVISION APPARATUS

[75] Inventor: Tetsuro Kurihara, Yokohama, Japan

[73] Assignee: Tokyo Shibaura Electric Co., Ltd., Kawasaki, Japan

[21] Appl. No.: 901,795

[22] Filed: May 1, 1978

[30] Foreign Application Priority Data

May 4, 1977 [JP] Japan .................................. 52-51516

[51] Int. Cl.² ............................................. H04N 5/32
[52] U.S. Cl. .................................. 358/111; 250/272; 250/320; 250/416 TV; 360/35
[58] Field of Search ................ 358/111; 250/272, 273, 250/274, 320, 322, 323, 36, 35, 416 TV; 360/35

[56] References Cited

U.S. PATENT DOCUMENTS

| | | | |
|---|---|---|---|
| 3,582,651 | 6/1971 | Siedband | 358/111 |
| 3,745,245 | 7/1973 | Yunde et al. | 358/111 |
| 3,919,467 | 11/1975 | Peuggot | 358/111 |

OTHER PUBLICATIONS

Itoh et al., —A Dose—Reducing TV Fluoroscopy System, Toshiba Review—Mar. 1973—Japan #79—pp. 19-24.
Muller et al., —Use of the Single-Image Store in General and Peroperative X-Ray Diagnostics—Medicamundi—vol. 20 #3-1975—pp. 108-113.
Sashin et al., —Electronic Radiography for Rapid Non-Invasive Intervention in Neurological Surgery—Medicine IV Spie, vol. 70, 1975—pp. 332-336.

*Primary Examiner*—John C. Martin
*Assistant Examiner*—Joseph A. Orsino, Jr.
*Attorney, Agent, or Firm*—Cushman, Darby & Cushman

[57] ABSTRACT

An X-ray television apparatus is provided with a mode switching circuit for switching from a one-shot radiographing mode to a hold radiographing mode and vice versa. In the one-shot radiographing mode, an X-ray picture obtained through a short time exposure to X-rays is recorded and reproduced. In the hold radiographing mode, an X-ray picture immediately before a continuous fluoroscoping operation is recorded and reproduced. In the one-shot mode, the record/reproduction is performed after a predetermined time from the turning-on of the operation switch. In the hold mode, the same is performed after a predetermined time from the turning-off of the operation switch.

6 Claims, 4 Drawing Figures

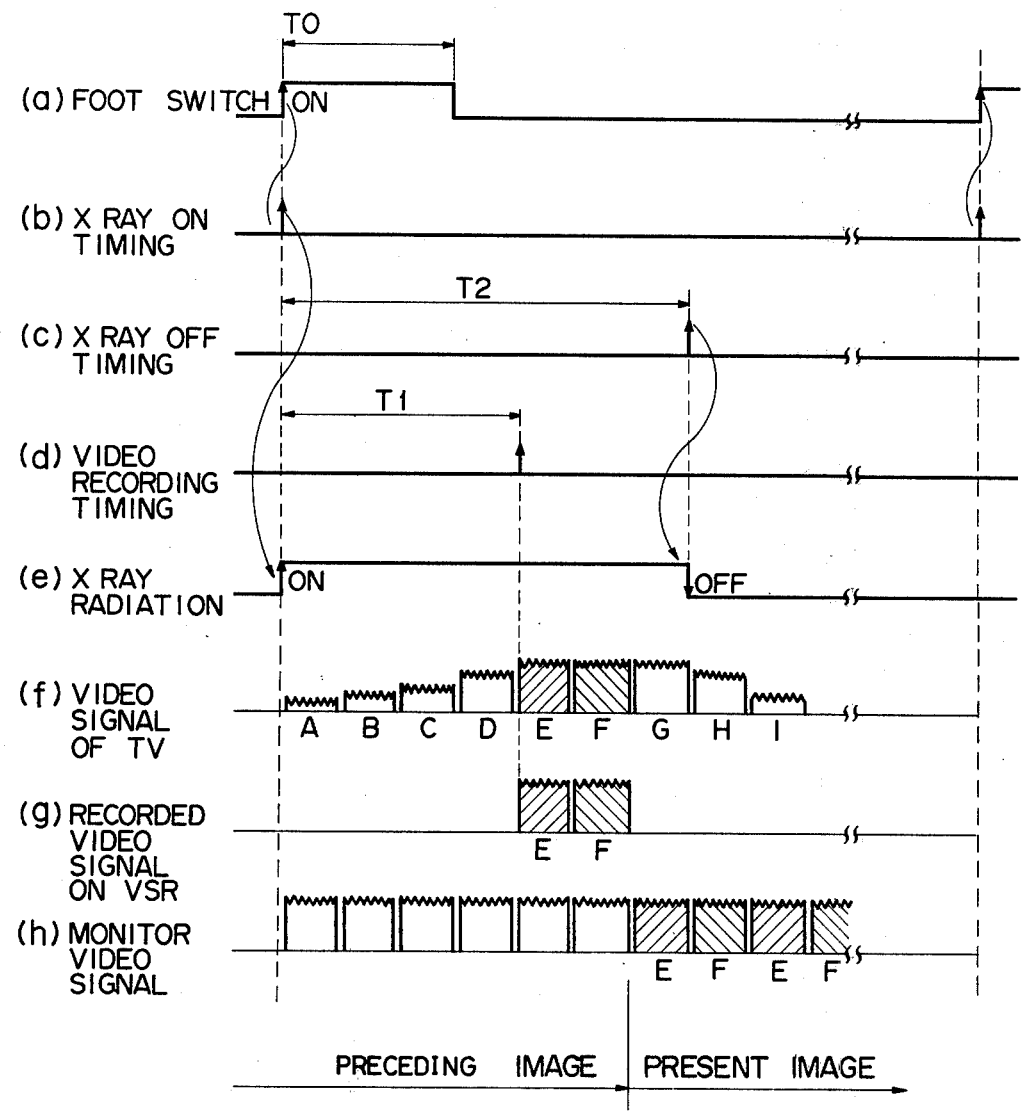

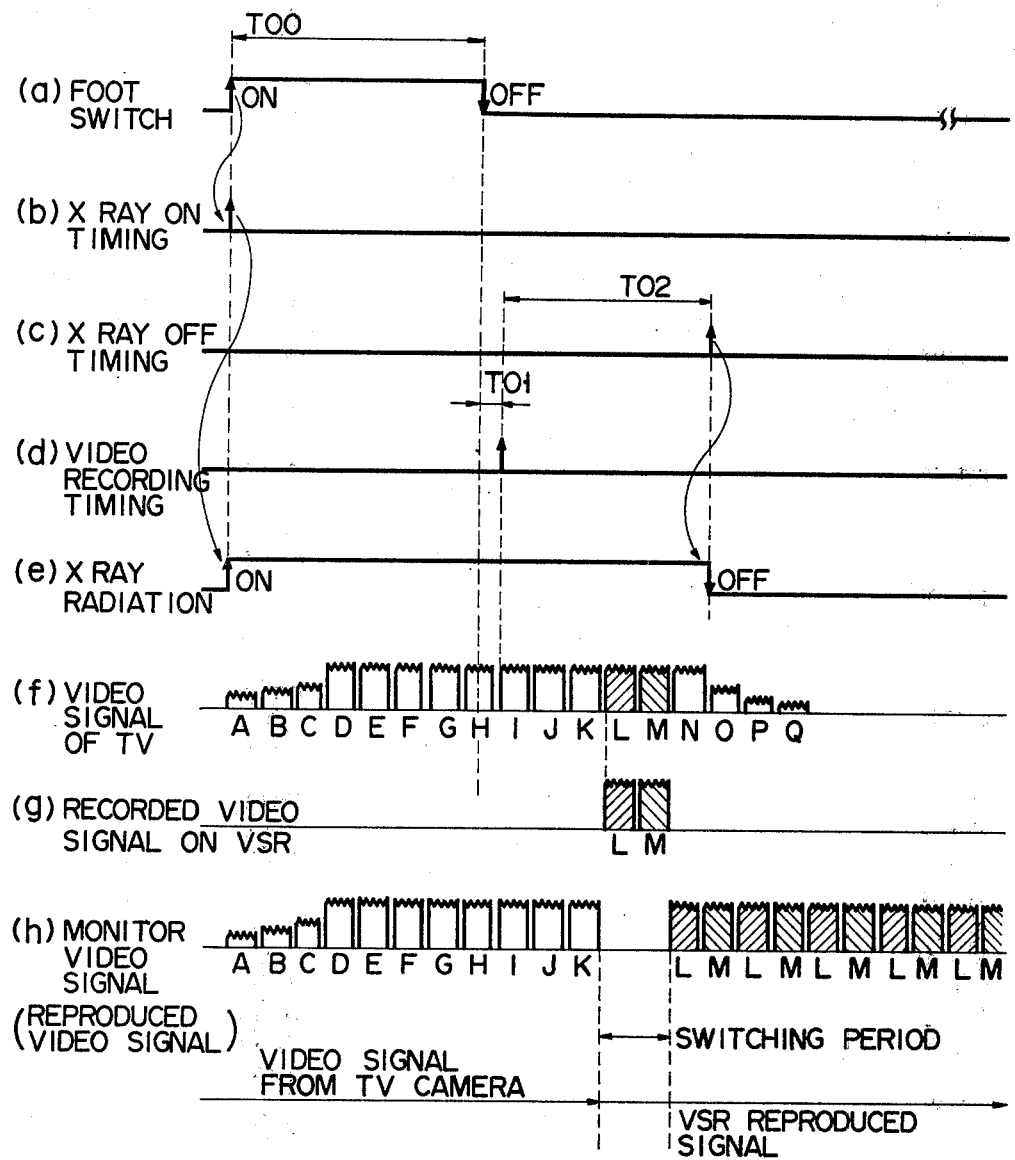

X-RAY TELEVISION APPARATUS

The invention relates to an X-ray television apparatus.

An X-ray television apparatus using a combination of an X-ray radiographing apparatus with a video tape recorder has lately been developed and put into practical use. The X-ray television apparatus is classified into two types; a one-shot type X-ray television apparatus for recording/reproducing an X-ray picture obtained through a short time exposure to X-ray, and a hold type X-ray television apparatus for recording/reproducing an X-ray picture immediately before a continuous fluoroscoping operation. The one-shot type X-ray television apparatus is suitable for surgical diagnosis by fluoroscoping quiescent objects, for example, the bone of hands or feet, and for the situation needing a small amount of the X-ray dosage. The hold type X-ray television apparatus is fitted for diagnosing moving objects such as hearts, blood vessels, gastrointestinal organs, etc.

The conventional X-ray television apparatus of this type is mono-functional, that is to say, it is operable as a mere one-shot or hold radiographing apparatus. For this, the utility of the conventional this type apparatus is poor.

Accordingly, an object of the invention is to provide an X-ray television apparatus which has both functions of one-shot radiographing and hold radiographing and is capable of selectively using the funtion.

According to the invention, there is provided an X-ray television apparatus comprising: means for radiating X-rays to an object to be examined; means for transducing the X-ray image of said object to a television signal, switching means for enabling said radiating means to operate; first timer means for producing a signal in accordance with the operation of said switching means; second timer means for producing a pulse at the end of the operation of said switching means; means for selecting one of said first and second timer means; means for separating a synchronizing signal from said television signal; means for producing a first signal in response to the pulse from the selected one of said first and second timer means and said synchronizing signal and a second signal after a predetermined time interval; means for energizing said X-ray radiating means in response to the operation of said switching means and deenergizing the same in response to said second signal; means for recording a desired part of said television signal in response to said first signal means for displaying selectively said television signal and said desired part of said television signal which are provided through said transducing means and recording means, respectively.

Other objects and features of the invention will be apparent from the following description taken in connection with the accompanying drawings, in which:

FIG. 3 shows a set of wave forms for illustrating the radiographing operation in the one-shot radiographing mode; and FIG. 4 shows a set of wave forms for illustrating the same in the hold radiographing mode.

Figure 1:
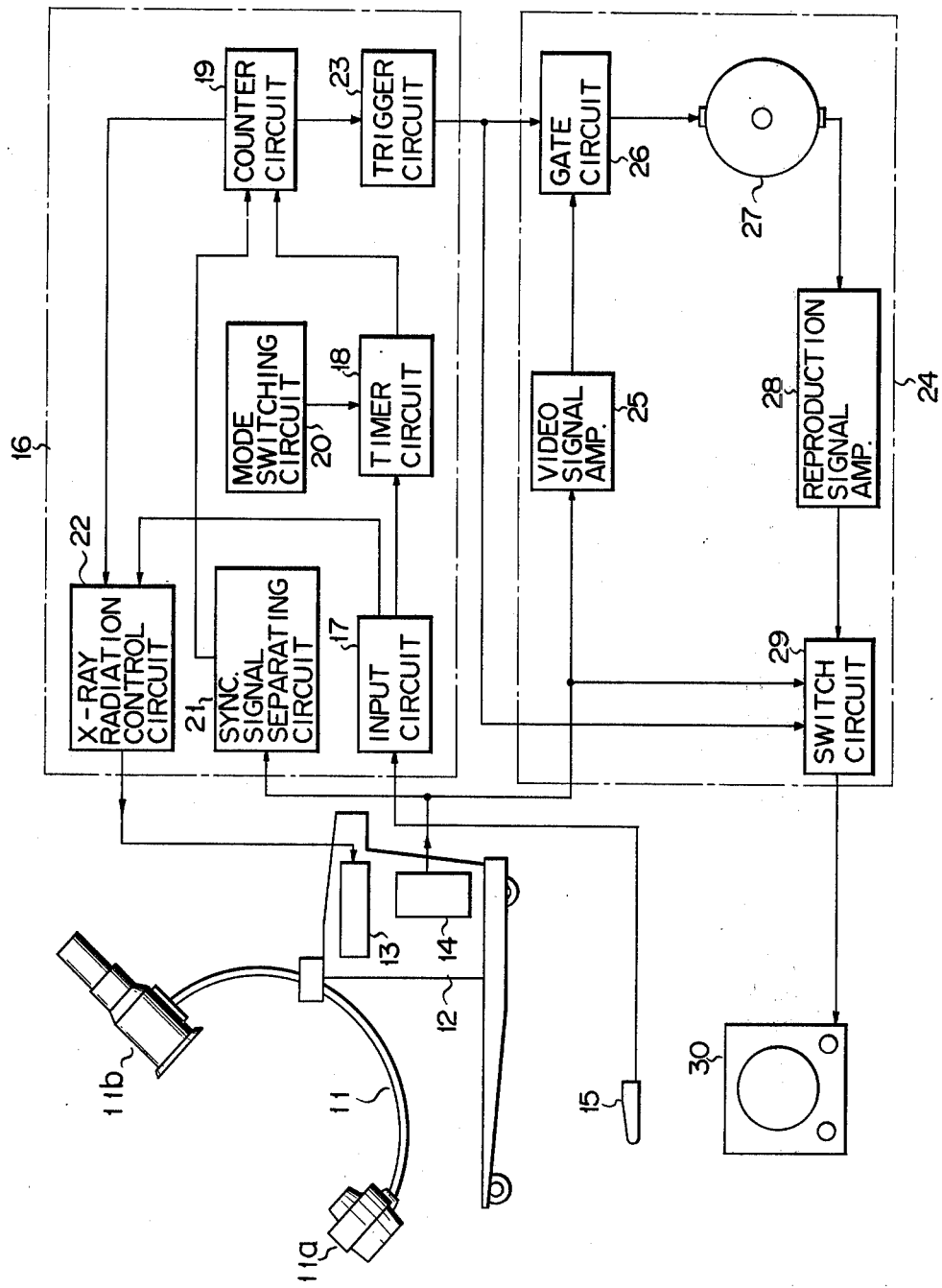
FIG. 1 shows a block diagram of an embodiment of an X-ray television apparatus according to the invention.

Referring now to FIG. 1, there is shown an X-ray television apparatus according to the invention. As shown, a fluoroscopic unit 11 is comprised of an X-ray source 11a and an optical apparatus having a television camera 11b. A console unit 12 is provided with an X-ray control unit 13 and a television camera control unit 14. An operation switch, e.g. a foot switch, designated by reference numeral 15 is coupled with an input circuit 17 in a mode switching unit 16 for switching a radiographing operation between a one-shot radiographing mode and a hold radiographing mode. The input circuit 17 is coupled at the output with a timer circuit 18. Receiving the output signals from a switching circuit 20 and the input circuit 17, the timer circuit 18 determines an radiation time of X-ray. The mode switching circuit selects the one-shot radiographing mode and the hold radiographing mode. The output of the timer circuit 18 and the output of a synchronizing signal separating circuit 21 are connected to a counter circuit 19. The counter circuit 19 synchronizes with a synchronizing signal derived from the synchronizing signal separating circuit 21 and, in response to the output signal of the timer circuit 18, it produces a recording instruction signal and an X-ray radiation stop signal. The synchronizing signal separating circuit 20 receives a television (video) signal from the television camera control unit 14, and separates the synchronizing signal from the television signal. The output of the counter circuit 19 is coupled with an X-ray radiation control circuit 22 and a trigger circuit 23. Upon receipt of the output signals of the counter circuit 19 and the input circuit 17, the X-ray radiation control circuit 22 produces an output signal to be directed to the X-ray control unit 13 for controlling the X-ray radiation and its ceasing. The trigger circuit 23 responds to the output signal of the counter circuit 19 to apply a picture trigger instruction signal to a video sheet recorder (VSR) device 24. The VSR device 24 is comprised of a video signal amplifier circuit 25 for amplifying a video signal from the television camera control unit 14 and a gate circuit 26 to gate-control the amplified video signal in response to the trigger signal from the trigger circuit 23. The output signal of the gate circuit 26 is coupled with a video sheet recorder 27. The video signal goes through the gate circuit 26 to be recorded on a magnetic disc of the video sheet recorder 27. A reproduction or play-back signal amplifier circuit 28 is connected to a video sheet recorder 27 in order to amplify the reproduction signal from the video sheet recorder 27. The output signal of the reproduction signal amplifier circuit 28 is connected to a television monitor 30 via a switch circuit 29. The switch circuit 29 operates in response to the trigger signal from the trigger circuit 23 to selectively apply the video signal from the reproduction amplifier circuit 28 and the video signal from the television camera unit 14, to a monitor television 30.

The invention is mainly directed to the mode switch control unit 16 for mode switching. Therefore, this unit will be further elaborated referring to FIG. 2. In the figure, the input circuit or operation switch circuit 17 includes an electromagnetic relay 17a connected in series with the foot switch 15 and having a first switch 17a1 with normally open contacts and NAND gates 17b and 17c which are connected at one input terminals with the normally open contacts. The other input terminal of the NAND gate 17b is connected to the output terminal of the NAND gate 17c. Similarly, the other input terminal of the NAND gate 17c is connected to the output terminal of the NAND gate 17b. A series circuit including resistors 17d and 17e is inserted between the one input terminals of the NAND gates 17b and 17c. A voltage +Vcc is applied to the node between the resistors 17d and 17e. The common contact of the first switch 17a1 is grounded. The output terminals of the NAND gates 17b and 17c are connected to the inputs of one-shot multivibrators 18a and 18b, respectively. The one-shot multivibrators 18a and 18b are included in the timer circuit 18. The reset terminals of the multivibrators 18a and 18b are respectively connected to the output terminals of inverters 20a and 20b in the mode switching circuit 20. The input terminals of the inverters 20a and 20b are connected to the fixed contacts of a switch 20c and to the power source +Vcc through resistors 20c and 20d. The movable contact of the switch 20c is earthed. The output terminals of the one-shot multivibrators 18a and 18b are connected to the input terminals of a NOR gate 18c. The output terminal of the NOR gate 18c is connected to the D input terminal of a D-type flip-flop 19a included in the counter circuit 19. The output terminal of the flip-flop 19a is connected to the T-input terminal of another D-type flip-flop 19b. The D-type flip-flop 19b is connected at the D-input to the power source +Vcc and at the output terminal to the R terminal of a counter 19c. The T terminal of the counter 19c is connected to the T-input terminal of the flip-flop 19a and the output terminal of the synchronizing signal separating circuit 21. The output terminal of the counter 19c is connected to the trigger circuit 23.

The D-type flip-flop is a circuit which has one input and the logical content of which is always put in one-bit (one-field) time preceding state, and in the sense that it is a delay circuit causing delay of one-bit time is called a delay (D) flip-flop. The true value table of the D-type flip-flop is as shown below.

tn: tn+1
D: Q
0: 0
1: 1

In the X-ray radiation control circuit 22, an inverter 22a is connected at the input to the output terminal of the NAND gate 17c and the input terminal of the multivibrator 18b, through a capacitor 22b. The input of the inverter 22a is earthed through a resistor 22c. The output of the inverter 22a is connected to one of the input terminals of a NAND gate 22d. The NAND gate 22d is connected at the other input terminal to the output of another NAND gate 22e and at the output to one of the input terminals of the NAND gate 22e. The NAND gate 22e is connected at the other input terminal to the output of the counter 19c in the counter circuit 19. The output terminal of the NAND gate 22d is connected to the cathode side of a photo-isolator 22f of which the anode side is connected to the power source +Vcc. An electromagnetic relay 22g is connected to the normally open contact of a second relay switch 17a2, through the output terminal of the photo-isolator 22f and a thyristor 22i. The relay 17a belongs to the switch circuit 11, as recalled. The normally open contact of a third relay switch of the relay 17a is connected to the power source +Vcc, through a delay relay 22j. The normally open contact 22ji of the delay relay 22j is connected in parallel with the normally open contact of the switch 17a2.

The operation of the thus constructed X-ray television apparatus will be given with operation modes of one-shot and hold radiographings.

The switch 20c of the mode switching circuit 20 is actuated to set up the one-shot radiographing mode. Upon this setting up, the one-shot multivibrator 18a is placed in a non-operation state, while the multivibrator 18b is placed in an operation mode. Under this condition, when the foot switch 15 is closed during the period of time T0 as shown in FIG. 3(a), the relay 17a is energized so that the normally open contacts of the relay switches 17a1 and 17a2 are closed but the normally close contact of the relay switch 17a3 is open. Upon the closing of the normally open contact of the relay switch 17a1, the NAND gate 17b produces an output pulse. The output pulse of the NAND gate 17c is applied to the first input terminal of the NAND gate 22d, through the capacitor 22b and the inverter 22a. Then, the NAND gate 22d produces an output pulse which in turn turns on the photo-isolator 22f. As a result, energizing current flows through the photo-isolator 22f, thyristor 22i, and the normally closed contact of the relay switch 17a2 into the electromagnetic relay 22g. Accordingly, the relay 22g is energized at the time point shown in FIG. 3(b) to close the normally open contact of the relay switch 22g1 which is connected to the X-ray control unit 13. Finally, the X-ray control unit 13 operates and starts radiation of X-rays, as shown in FIG. 3(e). At this time, the output pulse of the NAND gate drives the one-shot multivibrator 18b to produce a pulse signal (pulse width: 0.5 to 1 second). This pulse is applied to the D-terminal of the D-type flip-flop 19a by way of the NOR gate 18c. The flip-flop 19a produces an output pulse in response to the trailing edge of the pulse of the NOR gate 18c and in synchronism with the vertical synchronizing signal from the synchronizing signal separating circuit 21. The output pulse of the flip-flop 19a is applied to the T-terminal of the D-type flip-flop 19b. Then, the flip-flop 19b produces an output pulse in synchronism with the output pulse of the flip-flop 19a and the output pulse is applied to the counter 19c to set the same. When the counter 19 is set, it produces a recording instruction signal in synchronism with the vertical synchronizing signal from the synchronizing signal separating circuit 21. The recording instruction signal is generated after the time T1 from ON-time of the foot switch as shown in FIG. 3(d). The time period T1 corresponds to that from the start of the X-ray radiation to the time point at which the output video signal of a TV camera unit reaches a stationary state, as shown in FIG. 3(f). In the figure, A to H designate scanning fields, respectively. Two fields are combined to form one frame, i.e. one complete picture. When the VSR recording instruction signal is applied from the counter 19c to the trigger circuit 23, the trigger circuit 23 produces a trigger signal. The trigger signal is applied to the gate circuit 26 of the video sheet recorder device 24 shown in FIG. 1 to enable the gate circuit 26. The enabling of the gate circuit 26 permits the video signal from the video signal amplifier 25 to pass therethrough to the video sheet recorder 27 where it is recorded. In this case, the video signals E and F of two fields are recorded by the video sheet recorder 27 and these video signals are in the stationary state, as shown in FIG. 3(g). The video signals E and F recorded in the VSR are repeatedly reproduced, as shown in FIG. 3(h), and are amplified by the reproduction signal amplifier 28. The amplified signals are applied through the switch circuit 29 to the monitor television 30 where these are visualized in the form of an X-ray picture.

Returning again to FIG. 2, when the counter 19c carries out a predetermined number of counts, for example, three counts corresponding to three fields of the video signal, it generates an output pulse. The output pulse of the counter 19c is applied to the second input terminal of the NAND gate 22e as an X-ray OFF timing signal generated after a time T2 from the initiation (ON) of the X-ray radiation, as shown in FIG. 3(c). For this, the photo-isolator 22f is turned off and thus the electromagnetic relay 22g is deenergized to release the relay switch. Accordingly, the radiation of X-ray ceases after the time T2 from the start of X-ray radiation, as shown in FIG. 3(e). At this time, the output pulse of the counter 19c is also supplied to the reset terminal of the D flip-flop 19b to reset the same. The reset of the D flip-flop 19b results in the reset of the counter 19c. Nevertheless, the VSR device 24 continues its reproduction operation of the video signals E and F until the next X-ray radiation will be conducted. And the monitor television 30 continues its display of the X-ray image.

Then, the foot switch 15 is again closed as shown in FIG. 3(a). Upon this closing, the X-ray is radiated and a similar operation will be repeated.

The hold radiographing mode will be given.

Figure 2:
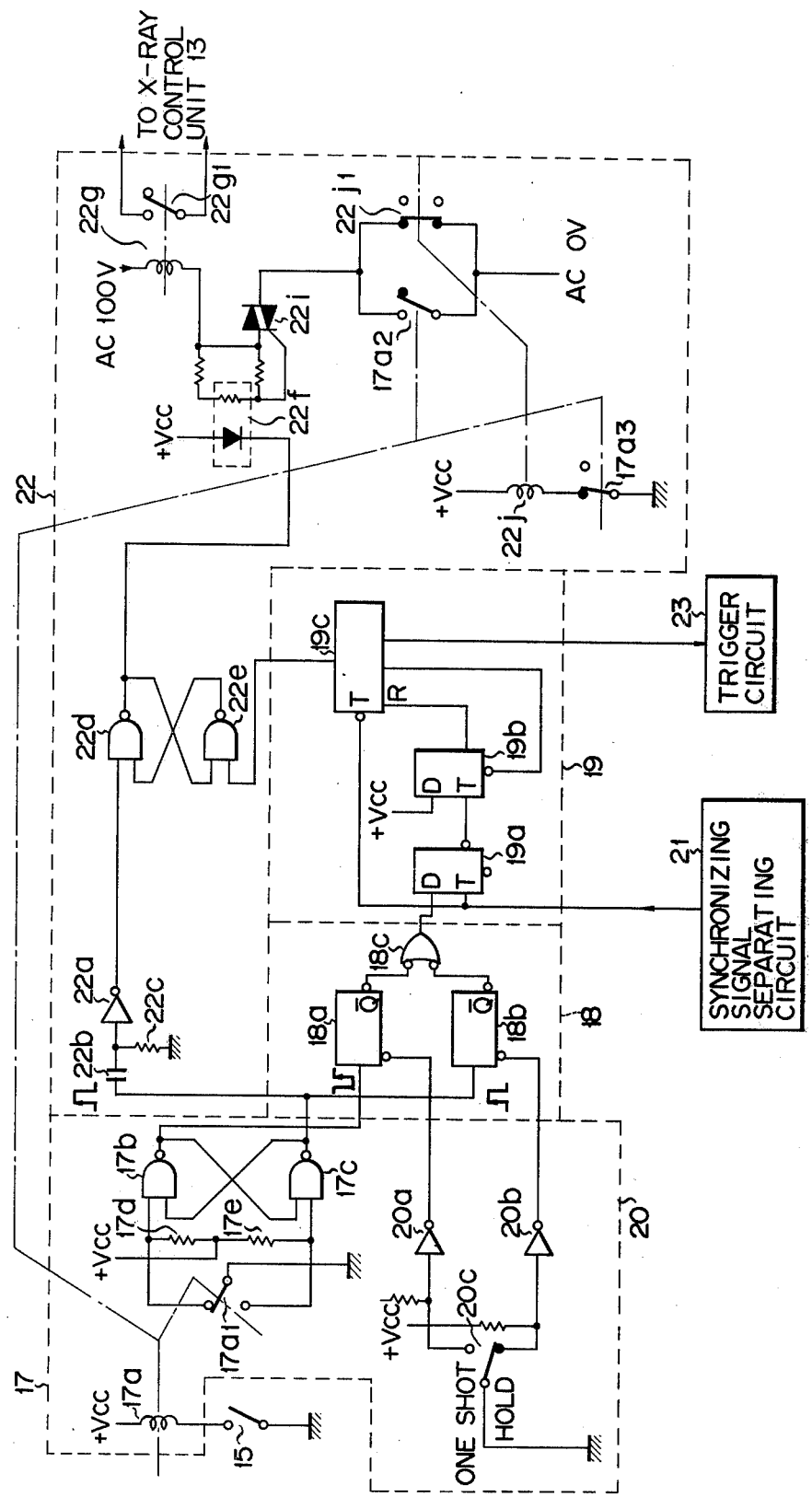
FIG. 2 shows a circuit diagram of a mode switching circuit for switching a radiographing mode between a one-shot radiographing mode and a hold radiographing mode.

The hold radiography is such that, in an ordinary continuous fluoroscopy, the final frame (two fields) of the X-ray television picture is recorded and reproduced. In this mode, the switch 20c of the switching circuit 20 in FIG. 2 is switched to the hold radiographing mode. This places the multivibrator 18a to be in the operation state. On the other hand, the multivibrator 18b is placed in the non-operation state. Under this condition, the foot switch 15 is assumed to be closed during the period of time To0, as shown in FIG. 4(a). As in the one-shot radiographing mode, the photo-isolator 22f is finally turned off in response to the output pulse of the NAND gate 18c. As a consequence, the electromagnetic relay 22g is energized and the radiation of the X-ray is initiated, see FIG. 4(b). At this time, the reverse pulse from the switch circuit 17 is applied to the multivibrator 18a so that no output pulse is produced from the multivibrator 18a. Additionally, the multivibrator 18b is in the non-operation state so that it produces no output pulse. This condition continues for the period To0 of the closing of the foot switch 15. In this period of time, the television camera unit 14 produces an X-ray fluoroscopic video signal, as shown in FIG. 4(f). The video signal goes through the switch circuit 29 to the monitor television 30 where the X-ray fluoroscopic picture is displayed.

After the period of time To0, the foot switch 15 is released to deenergize the electromagnetic relay 17a and to switch the relay switch 17a1. As a result, the output pulse of the NAND gates 17b and 17c are inversed. The multivibrator 18a produces an output pulse (pulse width: 100 to 200 milliseconds) in response to the output pulse of the NAND gate 17b. When the output pulse of the multivibrator 18a is applied to the counter circuit 19 through the NOR gate 18c, the counter 19c of the counter circuit 19 produces the VSR recording instruction signal after a time To1 from the turning-off of the foot switch 15, in synchronism with the synchronizing signal of the synchronizing signal separating circuit 21, as shown in FIG. 4(d). The recording instruction signal produced drives the trigger circuit 23 to produce a trigger signal which in turn enables the gate circuit 26. At this time, the trigger signal is applied to the switch circuit 29. The trigger signal switches the switch circuit 29 from the television camera unit 14 to the reproduction signal amplifier 28. During this switching period, the video signals L and M of two fields from the television camera unit 14 are applied to the video sheet recorder 27, through the video signal amplifier 25 and the gate circuit 26. The video signals L and M recorded are repeatedly reproduced and the reproduced ones are applied to the monitor television 30, through the reproduction amplifier 28 and the switch circuit 29. In this manner, the fluoroscopic image is displayed in the monitor television 30. The X-ray radiation is stopped at the termination of the period To2. The stopping of the X-ray radiation is performed through the same circuit operation as that of the one-shot radiographing mode.

As described above in the invention, the one-shot and hold radiographing are readily made through the switching operation of the switch circuit. This improves the operation of the X-ray television apparatus.

Finally, the protective relay circuit used in the above embodiment will be given. The protective relay circuit is comprised of the delay relay 22j connected in series to the normally open contact of the third relay switch 17a3 of the electromagnetic relay 17a of the input circuit 17 and a parallel circuit including the relay switches 17a2 and 22j1. The protective relay circuit is provided to prevent unnecessary radiation of X-ray when the circuitry in the X-ray radiation control circuit 22 erroneously operates due to noise or the like.

The delay time of the delay relay 22j is set up so as not to disturb the X-ray radiation period, e.g. 1 to 2 seconds. The operation of the protective relay circuit will be described relating to the one-shot radiographing mode and the hold radiographing mode.

In the one-shot radiographing mode, closing the foot switch 15 energizes the relay 17a to drive the relay switch 17a1, 17a2 and 17a3. Following this, the radiographing operation as mentioned relating to the one-shot radiographing operation, is conducted. The relay 22g is energized for a time period T2 and the X-ray is radiated for the same period. When the foot switch 15 is released within this period T2, the normally open contact of the relay switch 17a2 is released but the normally open contact of the relay switch 17a3 is closed. Through the operation of the contacts, the delay relay 22j is energized. Before the delay relay 22j is energized, the delay relay switch 22j1 is closed so that the energizing circuit of the relay 22g is held. After the delay time of the delay relay 22j, the relay switch 22ji is released. When the delay time of the delay relay is set up approximately the time period T2, if the photo-isolator 22f fails to turn off by some reason after the time period T2, the relay 22g is released to cease the X-ray radiation since the relay switch 22j1 is released after the delay time of the delay relay.

In the hold radiographing mode, the foot switch is closed and the fluoroscoping is made for the time period of Too. Then, releasing the foot switch opens the relay switch 17a2 of the relay 17a but the relay switch 17a3 is closed. As a result, the relay 22j is energized to close the relay switch 22j1 for a given delay time. This sustains the energization condition of the relay 22g. The delay relay switch 22j1 is released after a predetermined delay time longer than the time To0. Therefore, if the photo-isolator 22f fails to turn off by some reason, the circuit relating to the 22g is shut off after the relay switch 22j1 is released so that superfluous radiation of X-ray is prevented.

From the foregoing, it is seen that there is provided an X-ray television apparatus capable of properly select the one-shot or the hold radiographing mode, with a simple construction. The X-ray television apparatus of the invention is applicable for X-ray diagnosing moving and quiescent objects such as the bone and circulatory system of a human body.

A video tape recorder may be used in place of the video sheet recorder employed in the embodiment mentioned above. The time periods T1 and To1 and T2 and To2 for providing timings of issuance of the VSR recording instruction and stopping of X-ray radiation, may be properly set.

What is claimed is:

1. An X-ray television apparatus comprising:
    means for radiating X-rays to an object to be examined;
    means for transducing the X-ray image of said object to a television signal;
    switching means for enabling said radiating means to operate;
    first timer means for producing a signal in accordance with the operation of said switching means;
    second timer means for producing a signal at the end of the operation of said switching means;
    means for selecting one of said first and second timer means;
    means for separating a synchronizing signal from said television signal;
    means for producing a first signal in response to the signal from the selected one of said first and second timer means and said synchronizing signal and a second signal after a lapse of a predetermined time interval of said first signal;
    means for energizing said X-ray radiating means in response to the operation of said switching means and deenergizing the same in response to said second signal;
    means for recording a desired part of said television signal in response to said first signal; and means for displaying selectively said television signal and said desired part of said television signal which are provided through said transducing means and recording means, respectively.

2. An X-ray television apparatus according to claim 1, wherein said energizing-deenergizing means includes a protective circuit for deenergizing said X-ray radiating means to prevent unnecessary radiation of X-ray due to fault of said switching means.

3. An X-ray television apparatus according to claim 1, in which said switching means includes an operation switch and a circuit for producing a first start signal responsive to the turning on of said operation switch and a second start signal responsive to the turning-off of the same, said selecting means includes mode signal generating means which produces a first signal responsive to the selection of the one-shot mode and a second signal responsive to the selection of the hold mode, said first timer means includes a first one-shot multivibrator operable in response to the first signals from said switching means and said mode signal generating means, said second timer means includes a second one-shot multivibrator operable in response to the second signals from said switching means and said mode signal generating means, and said means for producing the first and second signals comprises a counter circuit generating the first signal in response to the output pulse of the selected one of said first and second multivibrator and generating the second signal in response to a fourth pulse after a count value corresponding to the predetermined time interval.

4. An X-ray television apparatus according to claim 1, in which said means for energizing and deenergizing the X-ray radiating means includes a gate circuit which produces an ON signal in response to the turning-on of said switching means and an OFF signal in response to the second signal of said means for producing the first and second signals, a photo-isolator which turns on in response to the ON signal of said gate circuit and turns off in response to the OFF signal of said gate circuit and relay means which operates in to the ON/OFF operation of said photo-isolator to open/close said X-ray generating circuit.

5. An X-ray television apparatus according to claim 1, in which said recording means includes a gate circuit which is enabled in response to the first signal from said means for producing the first and second signals to pass the television signal from said transducing means therethrough, a video sheet recorder which records the video signal after passing through said gate circuit and repeatedly reproduces the recorder television signal.

6. An X-ray television apparatus according to claim 5, in which said television signal is comprised of a plurality of field television signals and said video sheet recorder records the field television signal through said gate circuit.

* * * * *